US012697081B2

(12) United States Patent　　　(10) Patent No.:　US 12,697,081 B2
Kopel et al.　　　　　　　　　　　 (45) Date of Patent:　　　Aug. 4, 2026

(54) SYSTEMS AND METHODS OF VISUALIZING A MEDICAL DEVICE RELATIVE TO A TARGET

(71) Applicant: Covidien LP, Mansfield, MA (US)

(72) Inventors: Evgeni Kopel, Barkan (IL); Oren P. Weingarten, Hod-Hasharon (IL); Ariel Birenbaum, Raanana (IL); Michael E. Calcutt, Burnsville, MN (US)

(73) Assignee: Covidien LP, Mansfield, MA (US)

( * ) Notice: Subject to any disclaimer, the term of this patent is extended or adjusted under 35 U.S.C. 154(b) by 608 days.

(21) Appl. No.: 17/959,288

(22) Filed: Oct. 3, 2022

(65) Prior Publication Data

US 2023/0145801 A1　　May 11, 2023

Related U.S. Application Data

(60) Provisional application No. 63/277,738, filed on Nov. 10, 2021.

(51) Int. Cl.
　　*A61B 6/00*　　　　(2024.01)
　　*A61B 34/20*　　　(2016.01)
(52) U.S. Cl.
　　CPC .............. *A61B 6/487* (2013.01); *A61B 34/20* (2016.02); *A61B 2034/2046* (2016.02)
(58) Field of Classification Search
　　CPC . A61B 6/487; A61B 34/20; A61B 2034/2046; A61B 90/37; A61B 1/267;
　　　　　　　　　　　　　(Continued)

(56) References Cited

U.S. PATENT DOCUMENTS 8,494,612 B2　7/2013　Vetter et al.
8,821,376 B2　9/2014　Tolkowsky
　　　　　　　　(Continued)

FOREIGN PATENT DOCUMENTS

CN　　112451095 A　*　3/2021
CN　　112890953 A　*　6/2021　.............. A61B 34/20
EP　　　3127485 A1　*　2/2017　............... A61B 6/12

OTHER PUBLICATIONS

"Fully Automatic Catheter Segmentation in MRI with 3D Convolutional Neural Networks: Application to MRI-guided Gynecologic Brachytherapy", by Zaffino et al., published on Aug. 14, 2019 in Phys Med Biol., 64(16):165008. doi: 10.1088/1361-6560/ab2f47. PMID: 31272095; PMCID: PMC6726393 (Year: 2019).*

(Continued)

*Primary Examiner* — Matthew C Bella
*Assistant Examiner* — Daniel J. Santos
(74) *Attorney, Agent, or Firm* — Weber Rosselli & Cannon LLP

(57)　　　　　　ABSTRACT

Systems and methods of visualizing a current view of a tool relative to a lesion by processing current fluoroscopic images from a current fluoroscopic sweep occurring after an initial fluoroscopic sweep. The processing includes determining the locations and/or orientations of a tool and a lesion in a current 3D reconstruction of the current fluoroscopic images or in a subset of the current fluoroscopic images, generating a 3D rendering based on the locations and/or orientations of the tool and the lesion, and displaying the 3D rendering. The locations and/or orientations of the tool and the lesion may be obtained from a user interface enabling a user to mark the current locations and/or orientations in the current 3D reconstruction or in a subset of the current fluoroscopic images, or by segmenting the current (Continued)

3D reconstruction or a subset of the current fluoroscopic images.

20 Claims, 11 Drawing Sheets

(58) Field of Classification Search
CPC .... A61B 2017/00809; A61B 2034/107; A61B 2034/2048; A61B 2034/2051; A61B 2034/2061; A61B 2034/2063; A61B 2034/252; A61B 2090/373; A61B 2090/376; A61B 2090/3966; A61B 6/12; A61B 6/4441; A61B 6/465; A61B 6/547; A61B 6/466; A61B 2034/2055; A61B 2034/2068; A61B 34/10; A61B 5/06; A61B 6/032; A61B 6/504; A61B 34/30; A61B 5/062; A61B 5/066; A61B 6/485; A61B 6/5205; A61B 6/5258; G06N 3/09; G06T 15/00; G06T 17/00; G06T 19/003
USPC ......................................................... 382/128
See application file for complete search history.

(56) References Cited

U.S. PATENT DOCUMENTS

| | | | |
|---|---|---|---|
| 8,900,131 | B2 | 12/2014 | Chopra et al. |
| 10,896,506 | B2 | 1/2021 | Zhao et al. |
| 11,403,753 | B2 | 8/2022 | Holsing et al. |
| 2017/0209224 | A1 | 7/2017 | Walker et al. |
| 2019/0239838 | A1* | 8/2019 | Barak et al. ........... A61B 6/487 |
| 2019/0239961 | A1* | 8/2019 | Birenbaum et al. ... A61B 34/20 |
| 2020/0046436 | A1 | 2/2020 | Tzeisler et al. |
| 2020/0078101 | A1 | 3/2020 | Hunter et al. |
| 2020/0222018 | A1* | 7/2020 | Van Walsum et al. ...................... A61B 6/5205 |
| 2020/0245982 | A1* | 8/2020 | Kopel et al. ........... A61B 10/04 |
| 2020/0246079 | A1* | 8/2020 | Shevlev et al. ........ A61B 34/20 |
| 2020/0286267 | A1* | 9/2020 | Weingarten et al. ........................ G06T 11/008 |
| 2020/0297292 | A1* | 9/2020 | Alexandroni ........... A61B 6/12 |
| 2020/0315562 | A1 | 10/2020 | Weingarten et al. |

OTHER PUBLICATIONS

"A Novel Modified U-shaped 3-D Capsule Network (MUDCap3) for Stroke Lesion Segmentation from Brain MRI", by Sahayam et al., published on Dec. 3, 2020 in 2020 IEEE 4th Conference on Information & Communication Technology (CICT) (2020, pp. 1-6) (Year: 2020).*

"Three-Dimensional Guide-Wire Reconstruction From Biplane Image Sequences for Integrated Display in 3-D Vasculature", by Baert et al., published in Oct. 2003 in IEEE Transctions On Medical Imaging, vol. 22 (Year: 2003).*

Extended European Search Report issued in European Patent Application No. 22206347.1 dated Feb. 10, 2023.

Ma Hua et al: "Dynamic coronary roadmapping via catheter tip tracking in X-ray fluoroscopy with deep learning based Bayesian filtering", Medical Image Analysis, Oxford University Press, Oxford, GB, vol. 61, Jan. 11, 2020 (Jan. 11, 2020).

* cited by examiner

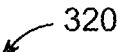
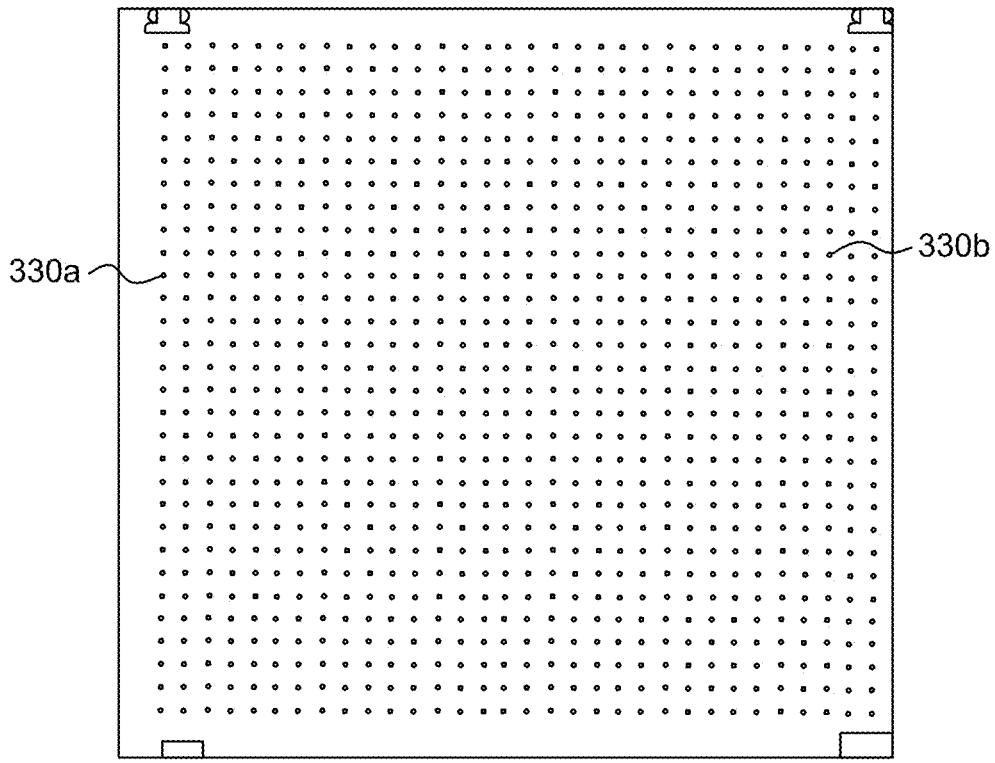
FIG. 3

400

410a

410b

410c

102

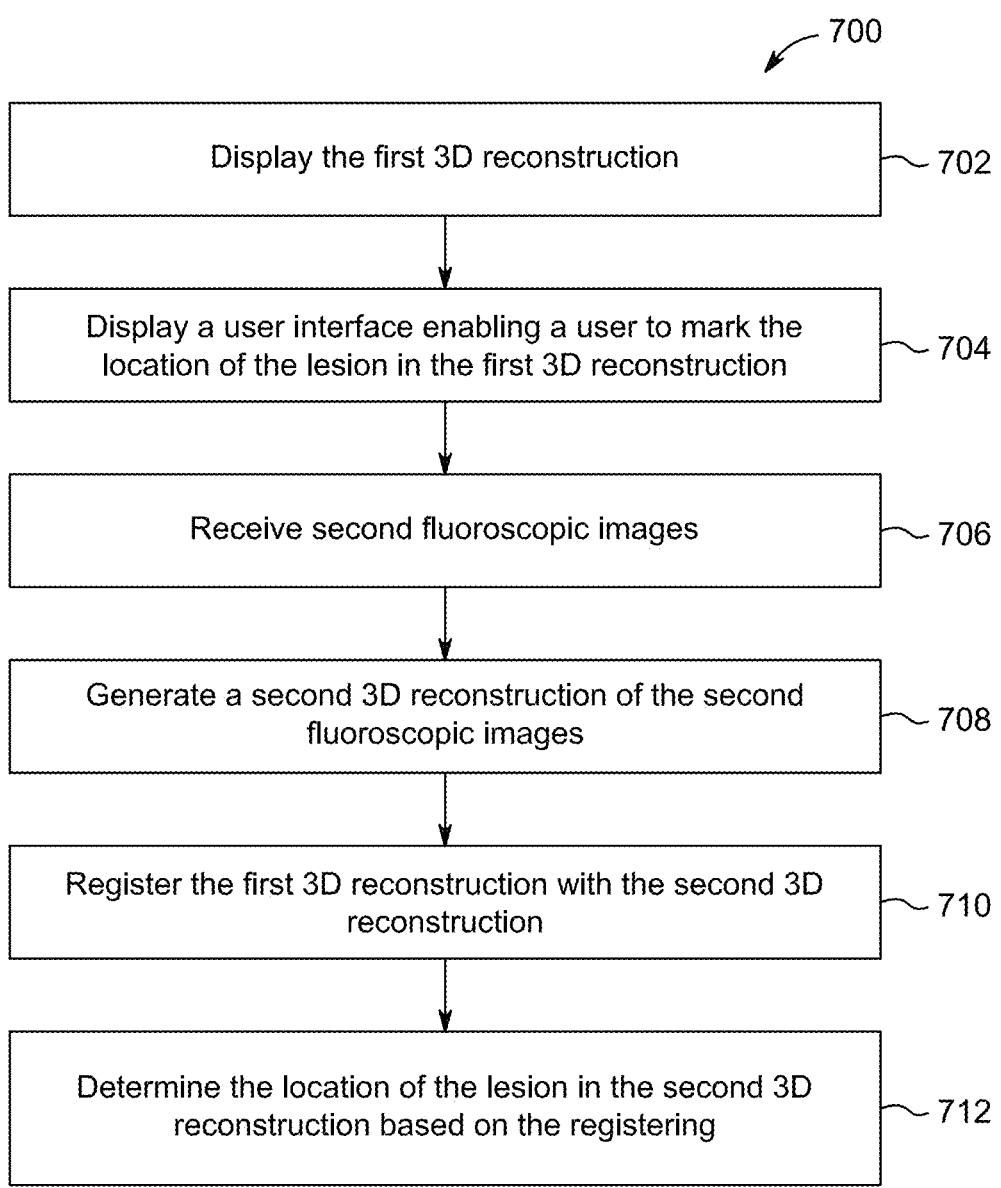

700

| Display the first 3D reconstruction | ~702 |

↓

| Display a user interface enabling a user to mark the location of the lesion in the first 3D reconstruction | ~704 |

↓

| Receive second fluoroscopic images | ~706 |

↓

| Generate a second 3D reconstruction of the second fluoroscopic images | ~708 |

↓

| Register the first 3D reconstruction with the second 3D reconstruction | ~710 |

↓

| Determine the location of the lesion in the second 3D reconstruction based on the registering | ~712 |

FIG. 7

SYSTEMS AND METHODS OF VISUALIZING A MEDICAL DEVICE RELATIVE TO A TARGET

CROSS-REFERENCE TO RELATED APPLICATIONS

This application claims the benefit of U.S. Application Ser. No. 63/277,738.

FIELD

This disclosure relates to the field of imaging, and particularly to the visualization of a current view of a medical device relative to a lesion using a three-dimensional (3D) rendering based on fluoroscopic images.

BACKGROUND

A fluoroscopic imaging device is commonly located in the operating room during navigation procedures. The standard fluoroscopic imaging device may be used by a clinician, for example, to visualize and confirm the placement of a medical device after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions. Furthermore, the fluoroscope image is only a two-dimensional (2D) projection. Thus, volumetric imaging is needed to navigate within the body safely and accurately.

SUMMARY

The techniques of this disclosure generally relate to visualizing the position of a medical tool relative to a lesion. In one aspect, this disclosure provides a method for causing display of a 3D rendering of a tool in a catheter relative to a lesion. The method includes receiving first fluoroscopic images from a fluoroscopic imaging device centered on the catheter, estimating a pose of the fluoroscopic imaging device for each of the first fluoroscopic images to obtain estimated poses, and generating a first three-dimensional (3D) reconstruction of the first fluoroscopic images using the estimated poses. The method further includes receiving locations of two points on the tool in the first 3D reconstruction and receiving a location of the lesion in the first 3D reconstruction. The method further includes generating a 3D rendering of the tool relative to the lesion based on the locations of two points on the tool and the location of the lesion, and causing display of the 3D rendering.

Further aspects of the disclosure may include one or more of the following features. The method may include causing display of the first 3D reconstruction and causing display of a user interface enabling a user to mark the locations of two points on the tool in the first 3D reconstruction. The method may include segmenting the tool in the first 3D reconstruction to obtain a segmented tool and determining the locations of two points on the tool based on the segmented tool. Segmenting the tool may include segmenting the tool using a neural network.

The method may include causing display of the first 3D reconstruction and causing display of a user interface enabling a user to mark the location of the lesion in the first 3D reconstruction. The method may include causing display of the first 3D reconstruction, causing display of a user interface enabling a user to mark the location of the lesion in the first 3D reconstruction, receiving second fluoroscopic images and generating a second 3D reconstruction of the second fluoroscopic images, registering the first 3D reconstruction with the second 3D reconstruction, and determining the location of the lesion in the second 3D reconstruction based on the registering. The method may include causing display of the first 3D reconstruction, causing display of a user interface enabling a user to mark a direction of a catheter tip in the first 3D reconstruction, generating a 3D rendering of the catheter relative to the tool and the lesion based on the direction of the catheter tip, and causing display of the 3D rendering of the catheter relative to the tool and the lesion.

The method may include segmenting a catheter in the first 3D reconstruction to obtain a segmented catheter, generating a 3D rendering of the catheter relative to the tool and the lesion based on the segmented catheter, and causing display of the 3D rendering of the catheter relative to the tool and the lesion.

The method may include causing display of a user interface enabling a user to adjust a view of the 3D rendering to a different angle. The method may include determining an orientation of an anatomical structure in the first 3D reconstruction, generating a 3D rendering of the anatomical structure at the orientation, and causing display of the 3D rendering of the anatomical structure at the orientation.

In another aspect, this disclosure provides a system for displaying a 3D rendering of a tool in a catheter relative to a lesion. The system includes a display, a processor in communication with the display, and a memory on which a neural network is stored. The memory further stores instructions, which, when executed by the processor, cause the processor to: receive first fluoroscopic images from a fluoroscopic imaging device centered on the catheter, estimate a pose of the fluoroscopic imaging device for each of the first fluoroscopic images to obtain estimated poses, generate a first three-dimensional (3D) reconstruction of the first fluoroscopic images using the estimated poses, apply a neural network to the first 3D reconstruction to determine a location and orientation of the tool in the first 3D reconstruction, receive a location of the lesion in the first 3D reconstruction, generate a 3D rendering of the tool relative to the lesion based on the location and orientation of the tool and the location of the lesion, and display the 3D rendering on the display.

Further aspects of the disclosure may include one or more of the following features. The instructions may cause the processor to: receive second fluoroscopic images, generate a second 3D reconstruction of the second fluoroscopic images, register the first 3D reconstruction, in which the lesion is marked, with the second 3D reconstruction, and determine the location of the lesion in the second 3D reconstruction based on the registering. The instructions may cause the processor to segment a shape of the lesion in the first 3D reconstruction to obtain a segmented shape of the lesion and generate the 3D rendering based on the segmented shape of the lesion.

In another aspect, this disclosure provides another method for causing display of a 3D rendering of a tool in a catheter relative to a lesion. The method includes receiving first fluoroscopic images from a fluoroscopic imaging device centered on the catheter, estimating a pose of the fluoroscopic imaging device for each of the first fluoroscopic images to obtain estimated poses, generating a first three-dimensional (3D) reconstruction of the first fluoroscopic images utilizing the estimated poses, receiving two second fluoroscopic images at angles separated by at least 15 degrees, receiving locations of two points on the tool in the two second fluoroscopic images, receiving a location of the lesion, generating a 3D rendering of the tool relative to the lesion based on the locations of two points on the tool and the location of the lesion, and causing display of the 3D rendering.

Further aspects of the disclosure may include one or more of the following features. The method may include causing display of the two second fluoroscopic images and causing display of a user interface enabling a user to mark the locations of two points on the tool in the two second fluoroscopic images. The method may include segmenting the tool in the two second fluoroscopic images by applying a neural network to the two second fluoroscopic images to obtain a segmented tool and determining the locations of two points on the tool based on the segmented tool.

The method may include causing display of the two second fluoroscopic images and causing display of a user interface enabling a user to mark the location of the lesion in the two second fluoroscopic images. The method may include causing display of the first 3D reconstruction, causing display of a user interface enabling a user to mark the location of the lesion in the first 3D reconstruction, registering the first 3D reconstruction with the two second fluoroscopic images, and determining the location of the lesion in the two second fluoroscopic images based on the registering. The method may include determining information regarding a position of the tool relative to the lesion and causing display of the information. The information may include a distance between a tip of the tool and a center of the lesion or a status of alignment between the tool and the lesion.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various exemplary aspects are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

FIG. 3 is a schematic illustration of a two-dimensional (2D) grid structure of sphere markers in accordance with the disclosure;

FIG. 7 is a flowchart of another method of the disclosure;

DETAILED DESCRIPTION

The disclosure is directed to systems and methods of visualizing the position of a medical device relative to a target in three-dimensional space. The systems and methods of the disclosure provide guidance to a clinician while the clinician advances a medical device towards a target, e.g., a lesion, and enable the clinician to confirm placement of the medical device in the target.

Figure 1:
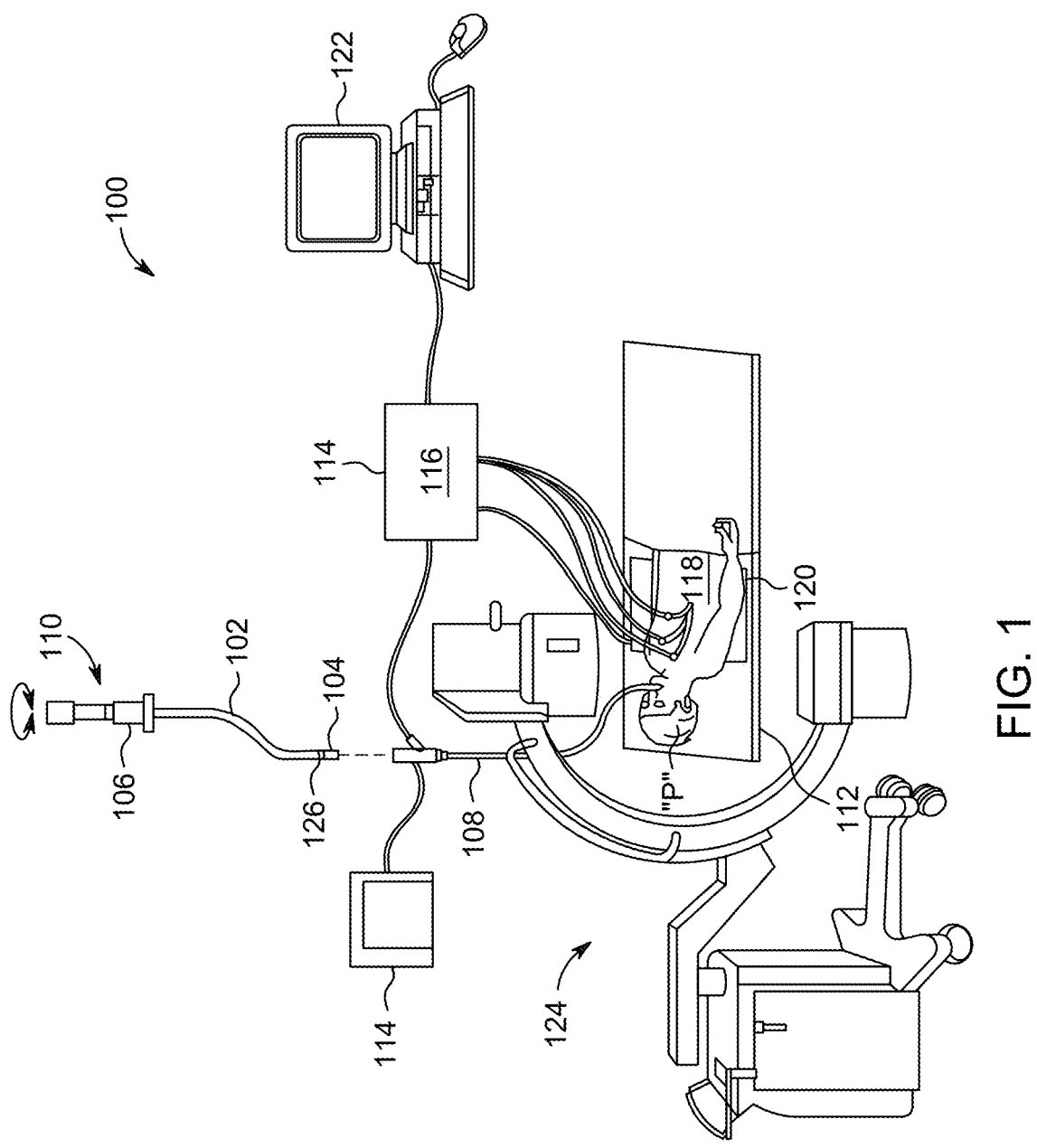
FIG. 1 is a schematic diagram of a system configured for use with the method of the disclosure.

FIG. 1 is a perspective view of an exemplary system for navigation of a medical device, e.g., a biopsy or treatment tool, to a target via airways of the lungs. One aspect of the system 100 is a software application for reviewing computed tomography (CT) image data that has been acquired separately from system 100. The review of the CT image data allows a user to identify one or more targets and plan a pathway to an identified target. This is typically referred to as a planning phase. Another aspect of the software application is a navigation phase which allows a user to navigate a catheter or other tool to a target (navigation phase) using a user interface and confirm placement of the catheter or a tool relative to the target. The target is typically tissue of interest for biopsy or treatment that was identified during the planning phase by review of the CT image data. Following navigation, a medical device, such as a biopsy tool or treatment tool, may be inserted into the catheter to obtain a tissue sample from the tissue located at, or proximate to, the target or to treat such tissue. The treatment tool may be selected to achieve microwave ablation, radio-frequency ablation, cryogenic ablation, chemical ablation, or other treatment mechanism of the target as preferred by the clinician.

One aspect of FIG. 1 is a catheter guide assembly 102 including a sensor 104 at a distal end. The catheter guide assembly 102 includes a catheter 106. In practice, catheter 106 is inserted into a bronchoscope 108 for access to a luminal network of the patient P. Specifically, catheter 106 of catheter guide assembly 102 may be inserted into a working channel of bronchoscope 108 for navigation through a patient's luminal network. If the system 100 is configured for electromagnetic navigation (EMN), a locatable guide (LG) 110, which may include the sensor 104 such as an electromagnetic (EM) sensor may be inserted into catheter 106 and locked into position such that sensor 104 extends a desired distance beyond the distal tip of catheter 106. However, it should be noted that the sensor 104 may be incorporated into one or more of the bronchoscope 108, catheter 106, or a biopsy or treatment tool, without departing from the scope of the disclosure.

If the catheter 106 is inserted into the bronchoscope 108, the distal end of the catheter 106 and LG 110 both extend beyond the distal end of the bronchoscope 108. The position or location and orientation of sensor 104 and thus the distal portion of LG 110, within an electromagnetic field can be derived based on location data in the form of currents produced by the presence of the EM sensors in a magnetic field, or by other means described herein. In some aspects, the methods of the disclosure may include visualizing and/or displaying the status information of the LG 110. Though the use of EM sensors and EMN are not required as part of this disclosure, their use may further augment the utility of the disclosure in endoluminal navigation (e.g., navigation of the lungs). As the bronchoscope 108, catheter 106, LG 110 or other tool could be used interchangeably or in combination herein, the term catheter will be used here to refer to one or more of these elements. Further, as an alternative to the use of EM sensors, flex sensors such as fiber Bragg sensors, ultrasound sensors, accelerometers, and others may be used in conjunction with this disclosure to provide outputs to the tracking system 114 for determination of the position of a catheter including without limitation the bronchoscope 108, catheter 106, LG 110, or biopsy or treatment tools, without departing from the scope of this disclosure.

System 100 may generally include an operating table 112 configured to support a patient P, a bronchoscope 108 configured for insertion through patient P's mouth into patient P's airways; tracking system 114 coupled to bronchoscope 108 (e.g., a video display, for displaying the video images received from the video imaging system of bronchoscope 108). If configured for EMN, system 100 may include a locating or tracking system 114 and a locating module 116, a plurality of reference EM sensors 118 and a transmitter mat 120 including a plurality of radio-opaque or partially radio-opaque markers (FIG. 3). Though shown in FIG. 3 as a repeating pattern of markers 330*a*, 330*b*, other patterns, including three dimensional markers at different relative depths in the transmitter mat 120, or a non-repeating pattern may be employed without departing from the scope of this disclosure.

Also included is a computing device 122 including software and/or hardware used to facilitate identification of a target, pathway planning to the target, navigation of a medical device to the target, and/or confirmation and/or determination of placement of catheter 106, or a suitable device therethrough, relative to the target. Computing device 122 may be similar to workstation 1001 of FIG. 10 and may be configured to execute the methods of the disclosure including the methods of FIGS. 2, 7, and 8. Computing device 122 may be any suitable computing device including a processor and storage medium, wherein the processor is capable of executing instructions stored on the storage medium as one or more applications. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed. Further details of the computing device are described in connection with FIG. 10, below.

Figure 11:
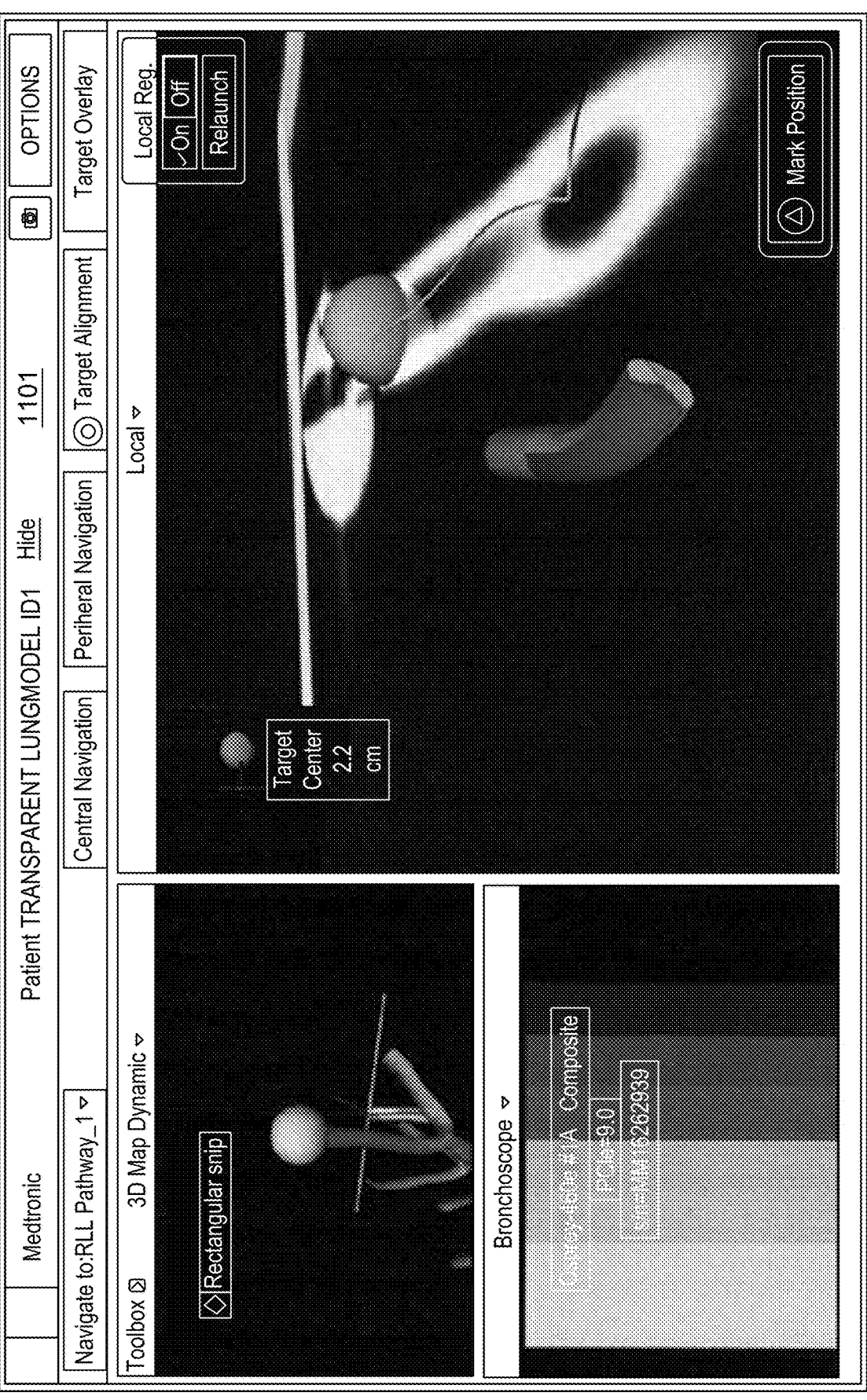
FIG. 11 is a user interface of an application for navigation through the airways in accordance with the disclosure.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images and CT image data sets acquired from CT scans are processed and assembled into a three-dimensional CT volume, which is then utilized to generate a three-dimensional model of patient P's airways. The three-dimensional model may be displayed on a display associated with computing device 122, or in any other suitable fashion. An example of such a user interface can be seen in FIG. 11. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s).

A fluoroscopic imaging device 124 capable of acquiring fluoroscopic or x-ray images or video of the patient P (which may be referred to generally as fluoroscopic image data sets) is also included in system 100. As shown in FIG. 1, the fluoroscopic imaging device 124 is in the form of a C-arm fluoroscope, which moves relative to the patient P so that fluoroscopic images may be acquired from different angles or perspectives relative to patient P to generate a sequence of fluoroscopic images, such as a fluoroscopic video. The fluoroscopic images, sequence of fluoroscopic images, or video captured by fluoroscopic imaging device 124 may be stored within fluoroscopic imaging device 124 or transmitted to computing device 122 for storage, processing, and display. The pose of fluoroscopic imaging device 124 relative to patient P and while capturing the fluoroscopic images may be estimated using the markers, pose estimation and image processing techniques described hereinbelow.

The markers may be incorporated into the transmitter mat 120, incorporated into the operating table 112, or otherwise incorporated into another appliance placed on or near the operating table 112 so that they can be seen in the fluoroscopic images. The markers are generally positioned under patient P and between patient P and a radiation source or a sensing unit of fluoroscopic imaging device 124. Fluoroscopic imaging device 124 may include a single imaging device or more than one imaging device.

Figure 2:
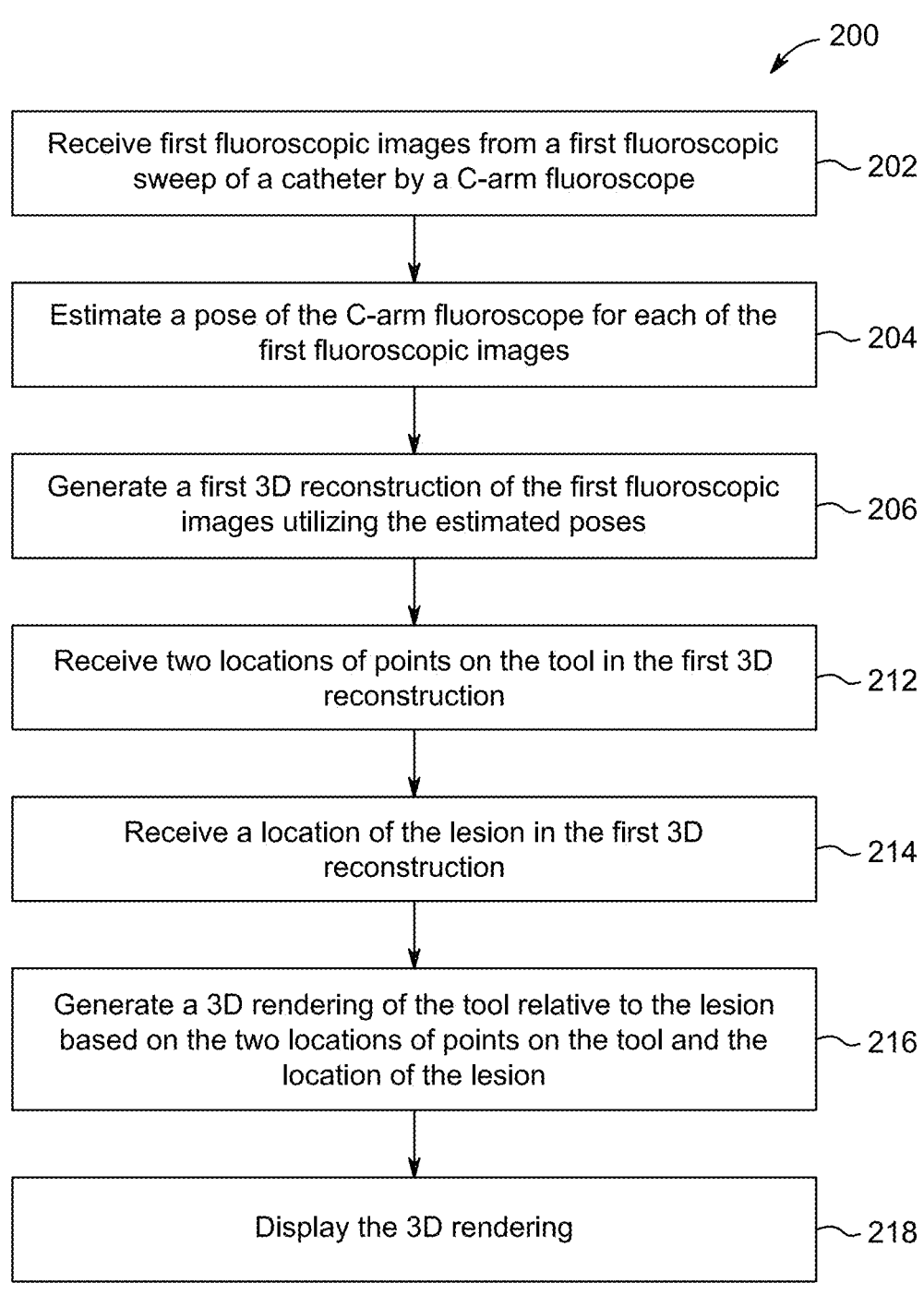
FIG. 2 is a flowchart of a method of the disclosure.

FIG. 2 is a flow chart of a method for visualizing a tool (e.g., a locatable guide (LG)) relative to a lesion and/or status information during navigation in accordance with this disclosure. In some cases, fluoroscopic navigation involves navigating a tool (e.g., an LG inside an extended working channel (EWC)) using local registration and re-navigating the tool using local registration correction. Thereafter, the clinician may want to confirm that the tool has reached or is aligned with the lesion. The tool may be the LG or a different tool inside the extended working channel such as a biopsy tool, a transbronchial access tool, or a therapeutic tool (e.g., a microwave ablation catheter). According to aspects of the disclosure, a second fluoroscopic navigation method is performed to confirm that the tool has reached the lesion without updating the registration or performing electromagnetic (EM) correction. The second fluoroscopic navigation method may not involve centering the fluoroscope on the catheter, setting the fluoroscopic image orientation, or configuring the fluoroscope settings because these functions are performed during the first fluoroscopic navigation method. In aspects, during the second fluoroscopic navigation method, the clinician can scroll through slices of the 3D reconstruction from the first fluoroscopic navigation method. In some aspects, no EM correction is performed during the second fluoroscopic navigation method.

As part of the procedure, a catheter 106 is navigated to a desired location in the patient "P." This may be done by following the pathway plan and using the EMN system described above, bronchoscopic imaging, or fluoroscopic imaging using fluoroscopic imaging device 124. Having navigated the catheter 106 to a desired location, a first fluoroscopic sweep of the catheter 106 is performed. The first fluoroscopic sweep acquires 2D fluoroscopic images at different angles as the fluoroscopic imaging device 124 rotates about the patient "P." Each 2D fluoroscopic image acquired by the fluoroscopic imaging device 124 includes the markers 330a, 330b as depicted in FIG. 3. At block 202, the first fluoroscopic images from the first fluoroscopic sweep of the catheter by the fluoroscopic imaging device 124 are received.

Figure 5:
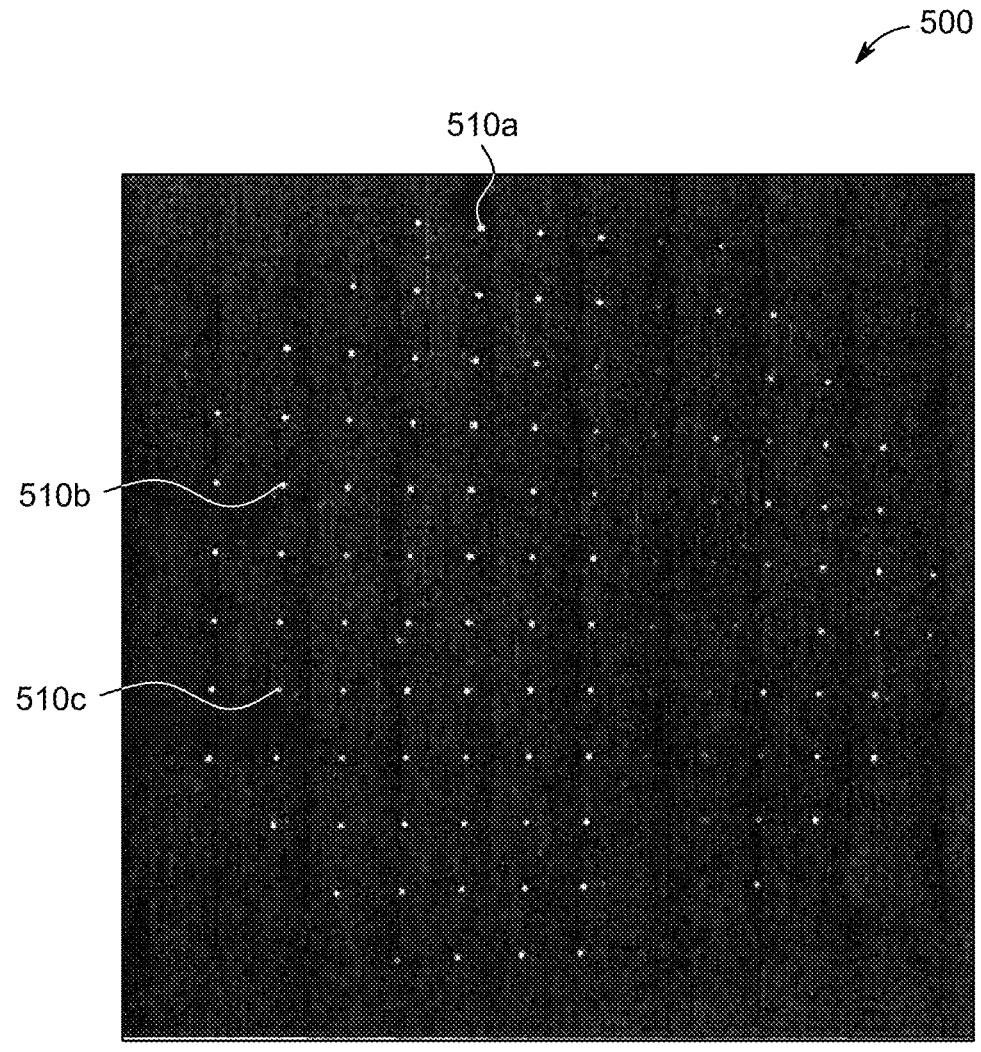
FIG. 5 is a probability map generated for the image of FIG. 4.

After receiving the first fluoroscopic images, a pose of the fluoroscopic imaging device 124 (e.g., a C-arm fluoroscope) is estimated for each of the first fluoroscopic images at block 204. The pose estimation may start with generating a probability map, an example of which is illustrated in FIG. 5. The probability map indicates the probability that a pixel of the image belongs to the projection of a marker of the transmitter mat 120.

Figure 4:
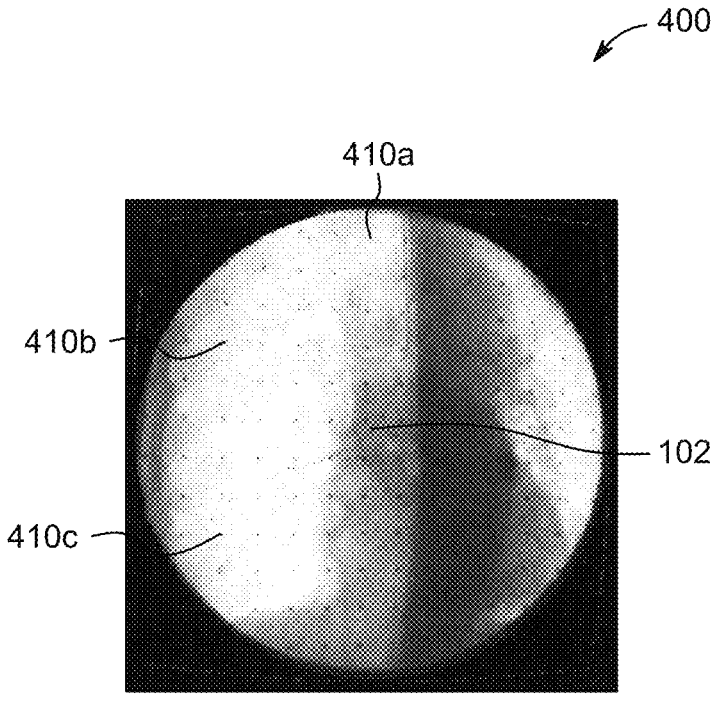
FIG. 4 shows an exemplary image captured by a fluoroscopic device of the disclosure.

FIG. 3 is a schematic illustration of a two dimensional (2D) grid structure of sphere markers 330a, 330b in accordance with the disclosure. FIG. 4 is an example of an image 400 captured by a fluoroscopic imaging device 124 of a patient in which the 2D grid structure of markers 330a, 330b are visible. The 2D grid structure of sphere markers 320 includes multiple sphere-shaped markers, such as sphere markers 330a and 330b, arranged in a two dimensional grid pattern. Image 400 includes a projection of a portion of 2D grid structure of sphere markers 330a, 330b and a projection of a catheter 106. The projection of 2D grid structure of sphere markers 330a, 330b on image 400 includes projections of the sphere markers, such as sphere marker 410a, 410b and 410c projections. A catheter guide assembly 102 is also observable in the image.

The probability map may be generated, for example, by feeding the image into a simple marker detector, such as a Harris corner detector, which outputs a new image of smooth densities, corresponding to the probability of each pixel to belong to a marker. Reference is now made to FIG. 5, which is a probability map 500 generated for image 400 of FIG. 4. Probability map 500 includes pixels or densities, such as densities 510a, 510b and 510c, which correspond accordingly to markers 410a, 410b and 410c. In some aspects, the probability map may be downscaled (i.e., reduced in size) in order to simplify the required computations.

Different candidates may be generated for the projection of the structure of markers on the image. The different candidates may be generated by virtually positioning the imaging device in a range of different possible poses. By "possible poses" of the fluoroscopic imaging device 124, it is meant three dimensional positions and orientations of the fluoroscopic imaging device 124. In some aspects, such a range may be limited according to the geometrical structure and/or degrees of freedom of the imaging device. For each such possible pose, a virtual projection of at least a portion of the markers is generated, as if the fluoroscopic imaging device 124 actually captured an image of the structure of markers while positioned at that pose.

The candidate having the highest probability of being the projection of the structure of markers on the image is identified based on the image probability map. Each candidate, i.e., a virtual projection of the structure of markers, may be overlaid or associated to the probability map. A probability score may be then determined or associated with each marker projection of the candidate. In some aspects, the probability score may be positive or negative, i.e., there may be a cost in case virtual markers projections falls within pixels of low probability. The probability scores of all of the markers' projections of a candidate may be then summed and a total probability score may be determined for each candidate. For example, if the structure of markers is a two dimensional grid, then the projection will have a grid form. Each point of the projection grid would lie on at least one pixel of the probability map. A 2D grid candidate receives the highest probability score if its points lie on the highest density pixels, that is, if its points lie on projections of the centres of the markers on the image. The candidate having the highest probability score may be determined as the candidate which has the highest probability of being the projection of the structure of markers on the image. The pose of the imaging device while capturing the image may be then estimated based on the virtual pose of the imaging device used to generate the identified candidate.

The above-described pose estimation process is one possible pose estimation process; however, those of skill in the art will recognize that other methods and processes of pose estimation may be undertaken without departing from the scope of the disclosure.

As noted above, the pose estimation process is undertaken for every image in the first fluoroscopic sweep. The result of the processing is a determination of the pose of the fluoroscopic imaging device 124 for each image acquired. At block 206, a first 3D reconstruction of the first fluoroscopic images is generated utilizing the estimated poses. The method 200 may include displaying the first 3D reconstruction and displaying a user interface enabling a user to mark the locations of two points on the tool in the first 3D reconstruction. The method 200 may include segmenting the tool in the first 3D reconstruction and determining the locations of two points on the tool based on the segmenting of the tool. Segmenting the tool may include segmenting the tool using a neural network. The method 200 may include displaying the first 3D reconstruction and displaying a user interface enabling a user to mark the location of the lesion in the first 3D reconstruction.

Where desired, the 3D reconstruction may be registered to a 3D model generated from a pre-operative CT scan. After navigating the tool, a 3D rendering may be generated based on a second fluoroscopic sweep to visualize the current location of the tool and/or the catheter relative to the lesion. To that end, second fluoroscopic images from a second fluoroscopic sweep may be obtained, and a second 3D reconstruction of the second fluoroscopic images may be generated.

For the visualization method, the location and orientation of the tool and the location of the lesion in the 3D reconstruction are obtained. The location and orientation of the tool may be obtained by prompting the user to mark the tool at two points in the 3D reconstruction. Additionally, or alternatively, the location and orientation of the tool may be obtained by executing software instructions for processing the 3D reconstruction to segment the tool using a suitable image processing method, such as a Convolutional Neural Network (CNN). The location of the lesion in the 3D reconstruction may be obtained by prompting the user to mark the lesion in the 3D reconstruction. Additionally, or alternatively, the location of the lesion may be obtained by registering the first 3D reconstruction with the second 3D reconstruction using a suitable method, such as a mutual information method. Since the user marked the lesion in the first reconstruction, the system knows the location of the lesion in the second reconstruction.

Figure 6:
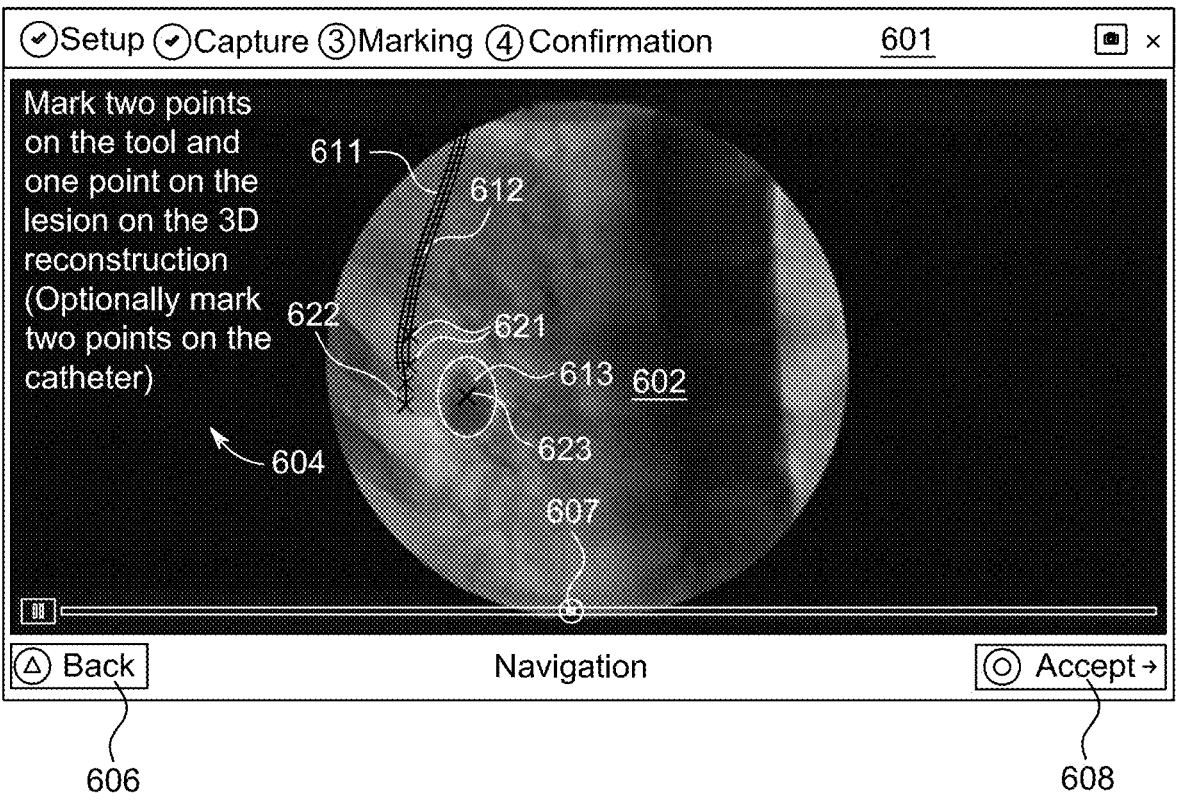
FIG. 6 depicts a user interface of the disclosure for marking a tool, a lesion, and/or a catheter in a 3D reconstruction in accordance with the disclosure.

A user interface may be displayed on the display of the computing device 122, in which a second 3D reconstruction is presented to a clinician and the clinician is asked to identify locations of two points on the tool and a location of a lesion in the second 3D reconstruction. For example, as illustrated in FIG. 6, user interface 601 is displayed on the display of the computing device 122, in which the second 3D reconstruction 602 is presented and a clinician is asked by instructions 604 to mark locations of two points on the tool 612 and a location of a lesion 613 in the second 3D reconstruction 602. The clinician may then use an input device 1010 (FIG. 10), e.g., a trackball or trackpad, to place markings 622 at two points on the tool 612 and a marking 623 at one location on the lesion 613. The instructions 604 may include an optional instruction to mark two points on the catheter 611. The clinician may then place markings 621 at two points on the catheter 611. In some aspects, the clinician may mark the tip of the catheter 611 and the direction of the tip of the catheter 611.

The user interface 601 also includes a scroll button 607, which the clinician may select and move left or right to change to a different slice of the second 3D reconstruction. The clinician may move the scroll button 607 to search for a slice of the second 3D reconstruction that gives the clinician the best view of the catheter 611, the tool 612, and the lesion 613, such that the clinician can accurately place the markings 621-623.

Additionally, or alternatively, the computing device 122 may execute an application that automatically segments the catheter 611 and/or the tool 612 to determine the location and orientation of the catheter 611 or the tip of the catheter 611 and/or the tool 612. In this additional or alternative aspect, the 3D rendering of the catheter 611 or the tip of the catheter 611 and/or the tool 612 relative to the lesion 613 is generated based on the segmented catheter 611 and/or tool 612. The segmentation may be performed using a suitable method such as a convolutional neural network (CNN).

The user interface 601 also includes a back button 606, which the clinician can select to return to previous screens of the user interface 601. For example, the clinician can select the "Back" button 606, which returns the user interface 601 to a "capture" screen, which may be used by the clinician to recapture second fluoroscopic images if the clinician finds that the existing second fluoroscopic images have poor quality. The user interface 601 also includes an "Accept" button 608, which the clinician can select to confirm placement of the markings 621-623 on the second 3D reconstruction 602.

After the clinician selects the accept button 608, the computing device 122 (FIG. 1) receives, at block 212, the locations of two points on the tool in the first 3D reconstruction and receives, at block 214, the location of the lesion in the first 3D reconstruction, which are determined based on the markings 622, 623. At block 216, a 3D rendering of the tool relative to the lesion is generated based on the locations of two points on the tool and the location of the lesion. At block 218, the 3D rendering is displayed on the display of the computing device 122. For example, the 3D rendering of the tool relative to the lesion may be displayed in the user interface 1101 of FIG. 11. In some aspects, the system software may segment the catheter and the tool on the 3D reconstruction or mark the catheter tip direction, and may also display the catheter or catheter tip. The system software may allow the user to view the 3D rendering from multiple angles. The anatomical orientation also be displayed.

At block 216, a 3D rendering of the catheter may also be generated based on the second 3D reconstruction. Alternatively, a line or a generic tool and/or catheter may be generated based on the second 3D reconstruction. The software application may identify which tool and/or catheter is rendered and displayed. The software application may identify the tool and/or catheter based on user input or may automatically identify the tool and/or catheter from the 2D fluoroscopic images. The 3D rendering may represent the tool and/or catheter as a 3D model that appears the same as the actual tool and/or catheter.

The 3D rendering of the lesion may be based on the planned target shape extracted from the pre-operative CT images in a planning application. The planning application may automatically segment the planned target shape or may display a user interface enabling a user to mark the planned target shape. In some aspects, the software application may adjust the position and/or shape of the lesion to match the position and/or shape of the lesion in the 3D reconstruction. As another option, the software application may extract the shape and/or position of the lesion directly from the 3D reconstruction.

For understanding the orientation of the anatomy, the software application may display axes or a rendering of the anatomy (e.g., ribs or airways) based on the 3D reconstruction or the pre-operative CT registered to the 3D reconstruction.

In addition to the 3D rendering, the confirmation view may also include statistics or status information regarding the position of the tool relative to the target (as the size of the target is known from the planning). For example, the status information may include whether the tool is located inside of the lesion, the distance of the tool to the center of the lesion, whether the tool is inside a central portion of the lesion, whether the tool is aligned with the lesion, whether an extrapolation of the tool reaches the lesion or a center portion of the lesion, and/or the distance of the extrapolation of the tool from the center of the lesion. In some aspects, at least some of the status information may be displayed on the 3D rendering. For example, the distance of the tool to the center of the lesion may be displayed in the 3D rendering as a line connecting the tip of the tool to the center of the lesion and text adjacent to the line indicating the distance.

The 3D rendering display window may include a user interface enabling a user to rotate the camera or to select views like gun barrel view/bullseye view along the tip of the catheter or select camera orientations, such as anterior-posterior view.

In some aspects, the location of the lesion may be determined automatically. For example, all or a portion of the method of FIG. 7 may be employed. At block 702, the first 3D reconstruction is displayed. At block 704, a user interface enabling a user to mark the location of the lesion in the first 3D reconstruction is displayed. After the lesion is marked in the first 3D reconstruction, second fluoroscopic images are received at block 706. At block 708, a second 3D reconstruction is generated from the second fluoroscopic images.

At block 710, the first 3D reconstruction is registered with the second 3D reconstruction. Then, at block 712, the location of the lesion in the second 3D reconstruction is determined based on the registering performed at block 710.

Figure 8:
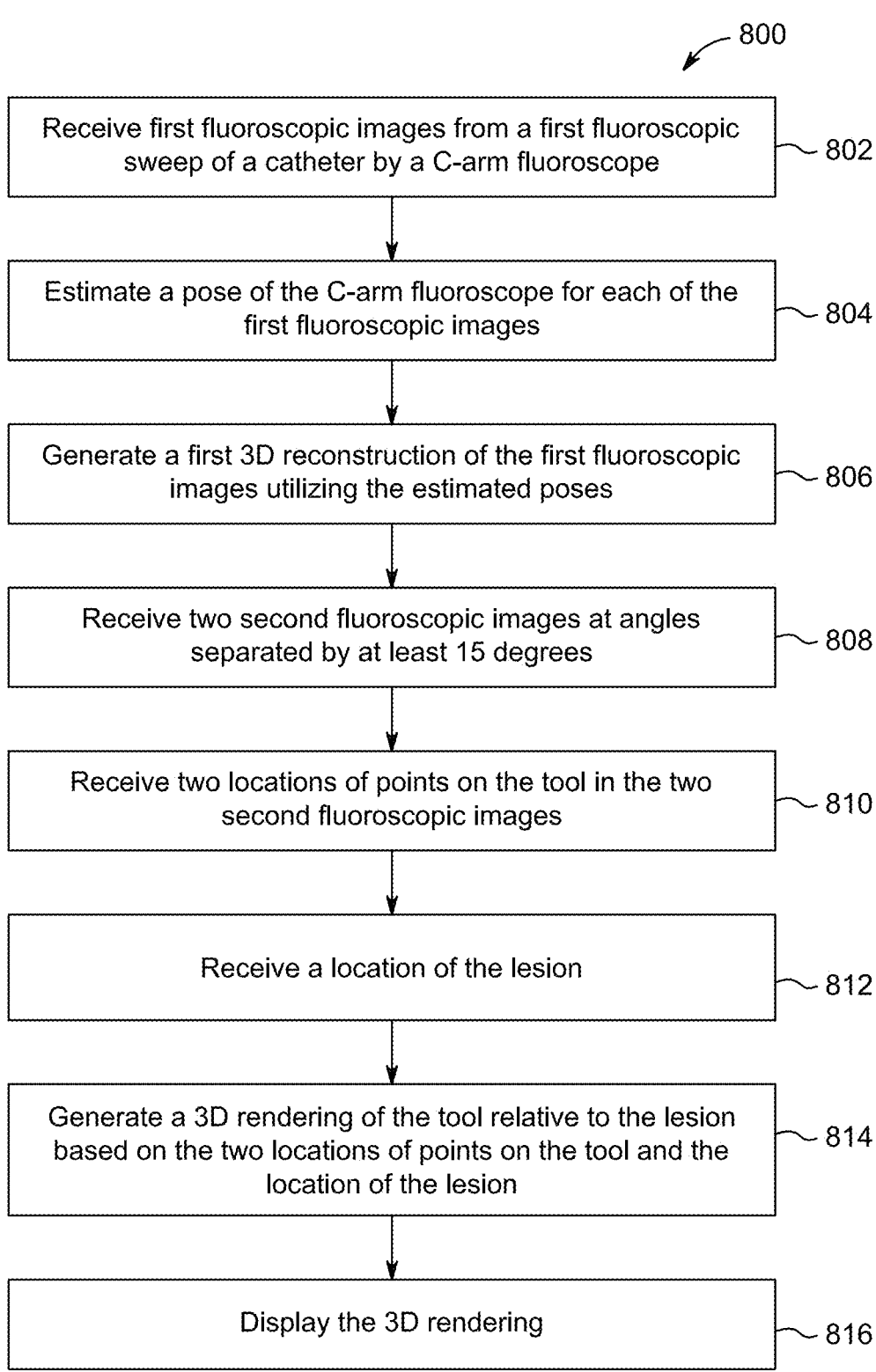
FIG. 8 is a flowchart of another method of the disclosure.

FIG. 8 illustrates an alternative method 800 of generating and displaying a 3D rendering of the tool relative to the lesion to assist the clinician with visualizing a surgical volume. Blocks 802-806 of the method 800 are the same as blocks 202-206 of the method 200. At block 808, two second fluoroscopic images at angles separated by at least 15 degrees are received. The two second fluoroscopic images are obtained by capturing one fluoroscopic image with the fluoroscopic imaging device positioned at a first angle and capturing another fluoroscopic image with the fluoroscopic imaging device positioned at a second angle that is separated by at least 15 degrees from the first angle.

Figure 9:
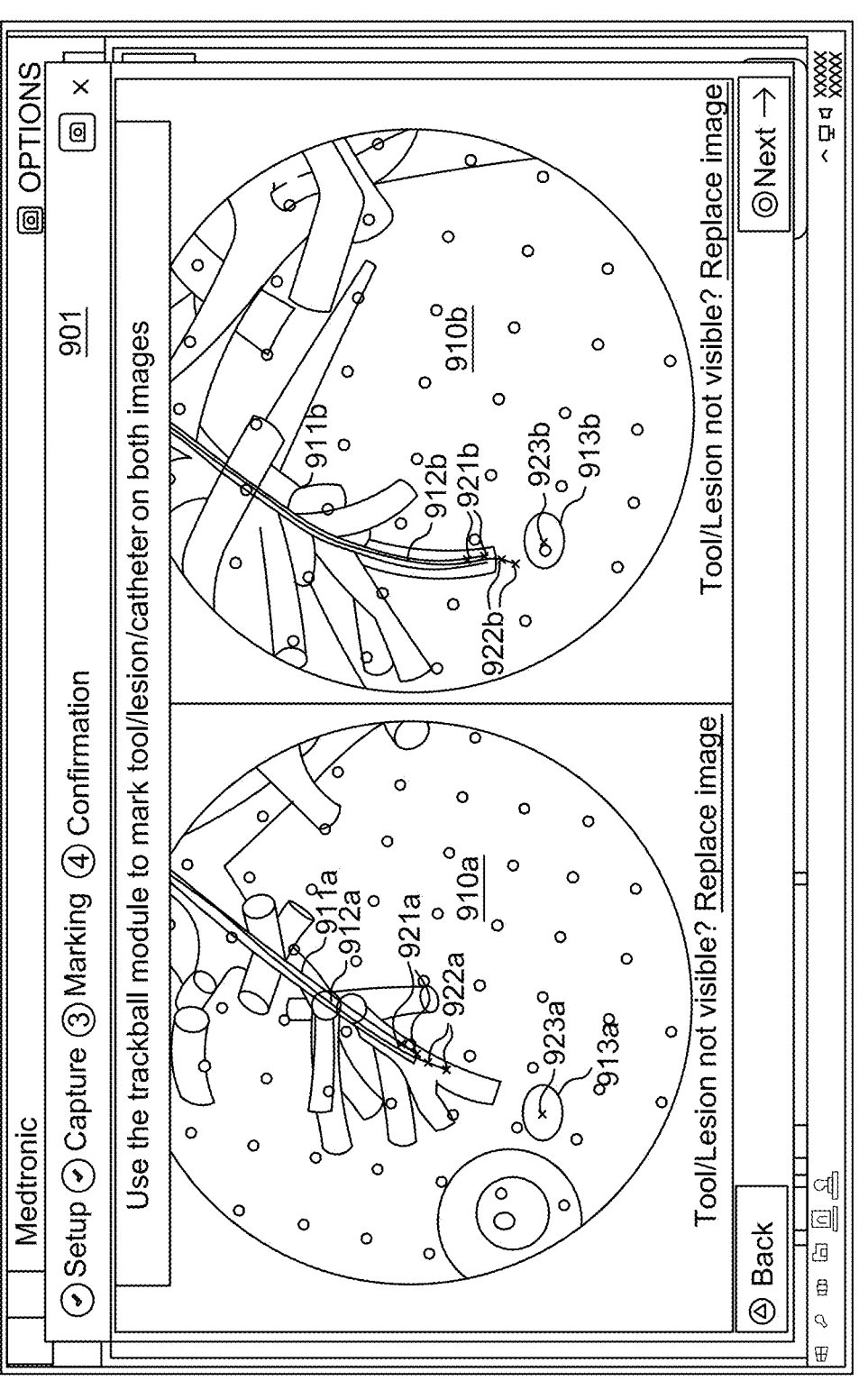
FIG. 9 depicts a user interface of the disclosure for marking a tool, a lesion, and/or a catheter in two current fluoroscopic images in accordance with the disclosure.

At block 810, locations of two points on the tool in the two second fluoroscopic images are received, and, at block 812, a location of the lesion is received. The locations of the points on the tool in the two second fluoroscopic image may be determined from marks placed by a clinician on the two second fluoroscopic images displayed in a user-interface. For example, as illustrated in FIG. 9, user interface 901 is displayed on the display of the computing device 122, in which two second fluoroscopic images 910*a*, 910*b* acquired during a second fluoroscopic sweep are presented and a clinician is asked to mark the location of two points in the fluoroscopic images 910*a*, 910*b*. The user interface 901 includes a message prompting the user to use the trackball module to mark the tool, the lesion or target, and the catheter in both second fluoroscopic images 910*a*, 910*b*. In the example of FIG. 9, marks 921*a*, 921*b* are placed on the catheter 911*a*, 911*b*; marks 922*a*, 922*b* are placed on the tool 912*a*, 912*b*; and marks 923*a*, 923*b* are placed on the tool 913*a*, 913*b*. The user interface 901 also includes messages asking whether the tool and lesion are visible in the second fluoroscopic images 910*a*, 910*b*. The user interface 901 also includes the hyperlinked text "Replace image", which the clinician can select to replace one or both of the second fluoroscopic images 910*a*, 910*b*, if the tool or lesion is not visible or is difficult for the clinician to see.

In aspects of the disclosure, the first fluoroscopic images are acquired before the medical procedure or at the beginning of the medical procedure, and the second fluoroscopic images are acquired during the medical procedure, such as while the tool 912 is being guided through the catheter 911 towards the lesion 913.

Alternatively, blocks 808-816 of method 800 may be replaced by blocks which include displaying the first 3D reconstruction, displaying a user interface enabling a user to mark the direction of a catheter tip in the first 3D reconstruction, generating a 3D rendering of the catheter relative to the tool and the lesion based on the direction of the catheter tip, and displaying the 3D rendering of the catheter relative to the tool and the lesion.

While the marking of the second fluoroscopic images is described here as manual, a portion of the catheter and/or tool may also be automatically detected using a segmentation process. For example, blocks 808-816 of method 800 may be replaced by blocks which include segmenting a catheter in the first 3D reconstruction, generating a 3D rendering of the catheter relative to the tool and the lesion based on the segmenting of the catheter, and displaying the 3D rendering of the catheter relative to the tool and the lesion.

The segmentation process to obtain the location and orientation of a portion of the catheter and/or tool may include cropping the second fluoroscopic images to produce images of, for example, one fourth or one half the size of the original second fluoroscopic images. Of course, the full image or other size cropped images may also be processed without departing from the scope of the disclosure. These cropped images define a region of interest and reduce the volume of data to be processed by the neural network.

A trained model for segmenting the catheter 611 or tool 612, or some other appropriate learning software or algorithm, which is in communication with the computing device 122 accesses 2D fluoroscopic images in which the location and orientation of the catheter 611 or tool 612 has been projected. The model may be a neural network that has been trained to identify a portion of the catheter 611 or the tool 612, or two locations on the catheter 611 or the tool 612 at or above a certain confidence level. This is done by allowing the neural network to analyze fluoroscopic images (e.g., from a fluoroscopic sweep) in which a catheter and/or a tool appears and allowing the neural network to perform image analysis to identify the location and orientation of at a least a portion of the catheter or tool in the patient's body. The actual location and orientation of the portion of the catheter and/or tool in each image or frame of the fluoroscopic sweep is known before being provided to the neural network for processing. A score is provided following each analysis of each frame by the neural network.

Over time and training, the neural network becomes more adept at distinguishing a portion of the catheter and/or the tool as distinct from the tissues of the patient or other material in which the catheter and/or tool is located when the images are acquired. The result is a model or neural network that, when used to analyze the image, identify the location and orientation of the portion of the catheter and/or tool with high confidence. Examples of neural networks that can be used to generate the model include a convolutional neural network or a fully connected network.

In order to improve the model or neural network, the model or neural network is trained to detect the location and orientation of a portion of the catheter and/or the tool. The neural network may be trained in a supervised manner. The training set may include thousands of fluoroscopy 2D images with coordinates of the catheter and/or tool marked manually. One method of training the neural network is to identify every frame of a fluoroscopic video as a main frame, and, for each main frame, identify at least one reference frame, and, in some aspects, two reference frames. These reference frames may be sequential immediately before and after the main frame, or at greater spacing (e.g., 10, 15, or 20 frames before and after). The reference frames assist in exploiting the temporal information in the fluoroscopic video to assist in estimating the coordinates of the portion of the catheter and/or tool. There should only be small changes in position between the main frame and the reference frames, so a detection at some distance outside of an acceptable range is determined to be a false positive by the neural network.

By repeating the processing of fluoroscopic images and detection of patterns which represent the catheter and/or tool, the neural network is trained to detect the portion of the catheter and/or tool. As noted above, the frames being analyzed may be cropped prior to this analysis by the neural network. Since the neural network analyzes multiple fluoroscopic images, the fluoroscopic images may be processed in parallel, which assists in regularization of the process and provides more information to the neural network to further refine the training.

During training of the neural network, a minimization of a loss function is employed. One such loss function is the comparison of the movement of the portion of the catheter and/or tool in successive frames. If the distance of movement exceeds an average movement between frames, then the score for that frame and its reference frames is reduced by the loss function. Heuristics can be employed to determine false detections. These false detections may occur when the portion of the catheter and/or tool is obscured in an image and cannot be easily detected. The false detections are a part of the training process, and as training continues the false detections are greatly reduced as the neural network learns the patterns of the portion of the catheter and/or tool in the images.

In instances where EMN system or another catheter and/or tool location is employed, the detected 3D location and orientation of the portion of the catheter and/or tool from the EMN system may be combined with the detected location and orientation of the portion of the catheter and/or tool derived by the model or neural network to provide a more robust determination of the location and orientation of the portion of the catheter and/or tool.

To improve the results of the segmentation described above, post processing techniques may be employed. For example, the segmentation of the tool 612 in the second fluoroscopic images or the second 3D reconstruction by the neural network may be given a confidence estimate. As a result, where the confidence estimate is low for the second fluoroscopic images or the second 3D reconstruction, the segmentation of the tool 612 may be rejected. If the segmentation of the tool 612 is rejected, the user interface 601 may be displayed to enable the clinician to manually mark the tool 612. The location and orientation of the tool 612 may be acquired from the second fluoroscopic images or the second 3D reconstruction in which segmentation has a high confidence.

The confidence estimate may be the result of a low signal to noise ratio in a particular second fluoroscopic image or the appearance of a major occlusion in the second fluoroscopic image. For example, a comparison of the main portion of a second fluoroscopic image with the median or average signal to noise ratio can reveal that the main portion of the second fluoroscopic image is an occlusion and therefore should be rejected. Other methods of detecting occlusions or determining a confidence estimate for a given second fluoroscopic image may be employed without departing from the scope of the disclosure.

At block 814, a 3D rendering of the tool relative to the lesion is generated based on the locations of two points on the tool or the location and orientation of the tool obtained from the segmentation process, and the location of the lesion. Then, at block 816, the 3D rendering is displayed to the clinician.

In some aspects, the method 800 may include displaying a user interface enabling a user to adjust the view of 3D rendering to a different angle. The method may include determining an orientation of an anatomical structure in the first 3D reconstruction, generating a 3D rendering of the anatomical structure at the determined orientation, and displaying the 3D rendering of the anatomical structure at the orientation.

Figure 10:
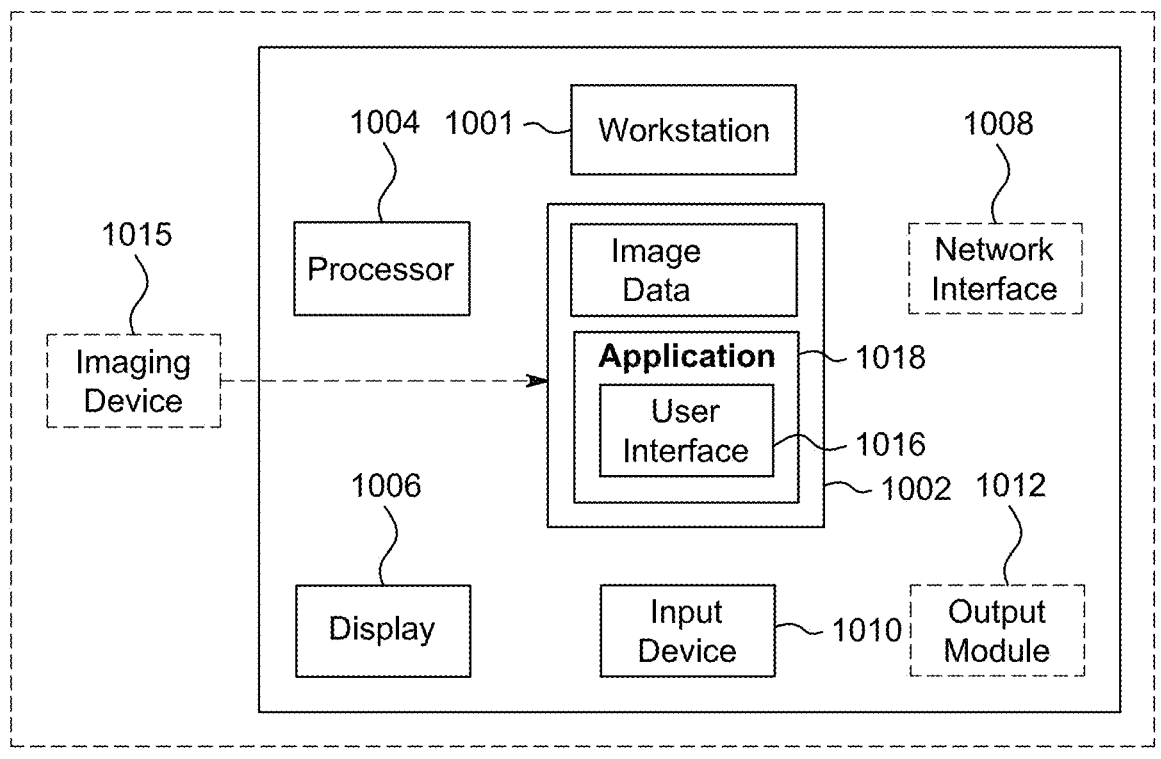
FIG. 10 is a schematic drawing of computer in accordance with the disclosure.

Reference is now made to FIG. 10, which is a schematic diagram of a system 1000 configured for use with the methods of the disclosure including the methods of FIGS. 2, 7, and 8. System 1000 may include a workstation 1001, and optionally connected to fluoroscopic imaging device 124 (FIG. 1). In some aspects, workstation 1001 may be coupled with fluoroscope 1015, directly or indirectly, e.g., by wireless communication. Workstation 1001 may include a memory 1002, a processor 1004, a display 1006 and an input device 1010. Processor 1004 may include one or more hardware processors. Workstation 1001 may optionally include an output module 1012 and a network interface 1008. Memory 1002 may store an application 1018 and image data 1014. Application 1018 may include instructions executable by processor 1004 for executing the methods of the disclosure including the methods of FIGS. 2, 7, and 8.

Application 1018 may further include a user interface 1016. Image data 1014 may include the CT scans, first and second fluoroscopic images, the generated first and second fluoroscopic 3D reconstructions and/or any other fluoroscopic image data and/or the generated one or more virtual fluoroscopy images. Processor 1004 may be coupled with memory 1002, display 1006, input device 1010, output module 1012, network interface 1008 and fluoroscope 1015. Workstation 1001 may be a stationary computing device, such as a personal computer, or a portable computing device such as a tablet computer. Workstation 1001 may embed multiple computer devices.

Memory 1002 may include any non-transitory computer-readable storage media for storing data and/or software including instructions that are executable by processor 1004 and which control the operation of workstation 1001 and, in some aspects, may also control the operation of fluoroscope 1015. Fluoroscopic imaging device 124 may be used to capture a sequence of fluoroscopic images based on which the fluoroscopic 3D reconstruction is generated and to capture a live 2D fluoroscopic view according to this disclosure. In an aspect, memory 1002 may include one or more storage devices such as solid-state storage devices, e.g., flash memory chips. Alternatively, or in addition to the one or more solid-state storage devices, memory 1002 may include one or more mass storage devices connected to the processor 1004 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1004. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1001.

Application 1018 may, when executed by processor 1004, cause display 1006 to present user interface 1016. User interface 1016 may be configured to present to the user a single screen including a three-dimensional (3D) rendering of the tool, the lesion, and/or the catheter of this disclosure. User interface 1016 may be further configured to display the lesion in different colors depending on whether the tool tip is aligned with the lesion in three dimensions.

Network interface 1008 may be configured to connect to a network such as a local area network (LAN) consisting of a wired network and/or a wireless network, a wide area network (WAN), a wireless mobile network, a Bluetooth network, and/or the Internet. Network interface 1008 may be used to connect between workstation 1001 and fluoroscope 1015. Network interface 1008 may be also used to receive image data 1014. Input device 1010 may be any device by which a user may interact with workstation 1001, such as, for example, a mouse, keyboard, foot pedal, touch screen, and/or voice interface. Output module 1012 may include any connectivity port or bus, such as, for example, parallel ports, serial ports, universal serial busses (USB), or any other similar connectivity port known to those skilled in the art.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method for causing display of a 3D rendering of a tool in a catheter relative to a lesion, comprising:

receiving first fluoroscopic images acquired during a fluoroscopic sweep of a fluoroscopic imaging device centered on the catheter;

estimating a pose of the fluoroscopic imaging device for each of the first fluoroscopic images to obtain estimated poses;

generating a first three-dimensional (3D) reconstruction of the first fluoroscopic images acquired during a fluoroscopic sweep of the fluoroscopic imaging device using the estimated poses;

applying a neural network to the first 3D reconstruction generated from the fluoroscopic sweep using the estimated poses to segment the tool within the first 3D reconstruction and obtain a segmented tool representation;

determining, from the segmented tool representation within the first 3D reconstruction, a first point corresponding to a distal end portion of the tool and a second point spaced from the first point to define an orientation of the tool;

receiving a location of the lesion within the first 3D reconstruction;

generating a 3D rendering of the segmented tool relative to the lesion within the first 3D reconstruction based on the first and second points and the location of the lesion; and causing display of the 3D rendering.

2. The method of claim 1, further comprising:

causing display of the first 3D reconstruction; and causing display of a user interface enabling a user to mark the locations of two points on the tool in the first 3D reconstruction.

3. The method of claim 1, further comprising determining the locations of two points on the tool based on the segmented tool.

4. The method of claim 1, further comprising:

causing display of the first 3D reconstruction; and causing display of a user interface enabling a user to mark the location of the lesion in the first 3D reconstruction.

5. The method of claim 1, further comprising:

causing display of the first 3D reconstruction;

causing display of a user interface enabling a user to mark the location of the lesion in the first 3D reconstruction;

receiving second fluoroscopic images;

generating a second 3D reconstruction of the second fluoroscopic images;

registering the first 3D reconstruction with the second 3D reconstruction; and determining the location of the lesion in the second 3D reconstruction based on the registering.

6. The method of claim 1, further comprising:

causing display of the first 3D reconstruction;

causing display of a user interface enabling a user to mark a direction of a catheter tip in the first 3D reconstruction;

generating a 3D rendering of the catheter relative to the tool and the lesion based on the direction of the catheter tip; and causing display of the 3D rendering of the catheter relative to the tool and the lesion.

7. The method of claim 1, further comprising:

segmenting a catheter in the first 3D reconstruction to obtain a segmented catheter;

generating a 3D rendering of the catheter relative to the tool and the lesion based on the segmented catheter; and causing display of the 3D rendering of the catheter relative to the tool and the lesion.

8. The method of claim 1, further comprising causing display of a user interface enabling a user to adjust a view of the 3D rendering to a different angle.

9. The method of claim 1, further comprising:

determining an orientation of an anatomical structure in the first 3D reconstruction;

generating a 3D rendering of the anatomical structure at the orientation; and causing display of the 3D rendering of the anatomical structure at the orientation.

10. The method of claim 1, wherein the first and second points are determined based on the segmented tool representation and are used to determine an orientation of the tool in the first 3D reconstruction.

11. A system for displaying a 3D rendering of a tool in a catheter relative to a lesion, comprising:

a display;

a processor in communication with the display; and a memory having stored thereon a neural network and instructions, which when executed by the processor, cause the processor to:

receive first fluoroscopic images acquired during a fluoroscopic sweep of a fluoroscopic imaging device centered on the catheter;

estimate a pose of the fluoroscopic imaging device for each of the first fluoroscopic images to obtain estimated poses;

generate a first three-dimensional (3D) reconstruction of the first fluoroscopic images acquired during the fluoroscopic sweep using the estimated poses;

apply a neural network to the first 3D reconstruction to segment the tool within the first 3D reconstruction and obtain a segmented tool representation and to determine a location and orientation of the segmented tool representation in the first 3D reconstruction by determining, from the segmented tool representation within the first 3D reconstruction, a first point corresponding to a distal end portion of the tool and a second point spaced from the first point to define an orientation of the tool;

receive a location of the lesion in the first 3D reconstruction;

generate a 3D rendering of the segmented tool relative to the lesion within the first 3D reconstruction based on the location and orientation of the segmented tool in the first 3D reconstruction and the location of the lesion; and display the 3D rendering on the display.

12. The system of claim 11, wherein the instructions further cause the processor to:

receive second fluoroscopic images;

generate a second 3D reconstruction of the second fluoroscopic images;

register the first 3D reconstruction, in which the lesion is marked, with the second 3D reconstruction; and determine the location of the lesion in the second 3D reconstruction based on the registering.

13. The system of claim 12, wherein the instructions further cause the processor to:

segment a shape of the lesion in the first 3D reconstruction to obtain a segmented shape of the lesion; and generate the 3D rendering based on segmented shape of the lesion.

14. A method for causing display of a 3D rendering of a tool in a catheter relative to a lesion, comprising:

receiving first fluoroscopic images acquired during a fluoroscopic sweep of a fluoroscopic imaging device centered on the catheter;

estimating a pose of the fluoroscopic imaging device for each of the first fluoroscopic images to obtain estimated poses;

generating a first three-dimensional (3D) reconstruction of the first fluoroscopic images acquired during the fluoroscopic sweep utilizing the estimated poses;

receiving two second fluoroscopic images at angles separated by at least 15 degrees;

registering the first 3D reconstruction with the two second fluoroscopic images;

determining a location of the lesion in the two second fluoroscopic images based on the registering;

segmenting the tool within the first 3D reconstruction to obtain a segmented tool representation by applying a neural network to the first 3D reconstruction;

determining, from the segmented tool representation within the first 3D reconstruction, a first point corresponding to a distal end portion of the tool and a second point spaced from the first point to define an orientation of the tool;

receiving a location of the lesion within the first 3D reconstruction;

generating a 3D rendering of the segmented tool relative to the lesion based on the first and second points and the determined location of the lesion; and causing display of the 3D rendering.

15. The method of claim 14, further comprising:

causing display of the two second fluoroscopic images; and causing display of a user interface enabling a user to mark the locations of two points on the tool in the two second fluoroscopic images.

16. The method of claim 14, further comprising determining the locations of two points on the tool based on the segmented tool.

17. The method of claim 14, further comprising:

causing display of the two second fluoroscopic images; and causing display of a user interface enabling a user to mark the location of the lesion in the two second fluoroscopic images.

18. The method of claim 14, further comprising:

causing display of the first 3D reconstruction;

causing display of a user interface enabling a user to mark the location of the lesion in the first 3D reconstruction;

registering the first 3D reconstruction with the two second fluoroscopic images; and determining the location of the lesion in the two second fluoroscopic images based on the registering.

19. The method of claim 14, further comprising:

determining information regarding a position of the tool relative to the lesion; and causing display of the information.

20. The method of claim 19, wherein the information includes a distance between a tip of the tool and a center of the lesion or a status of alignment between the tool and the lesion.

* * * * *